United States Patent [19]
Kahn et al.

[11] Patent Number: 5,859,184
[45] Date of Patent: Jan. 12, 1999

[54] ALPHA-HELIX MIMETICS AND METHODS RELATING THERETO

[75] Inventors: Michael Kahn, Kirkland; Hwa-Ok Kim, Redmond; Jan Urban, Kirkland, all of Wash.

[73] Assignee: Molecumetics Ltd., Bellevue, Wash.

[21] Appl. No.: 846,431

[22] Filed: Apr. 30, 1997

Related U.S. Application Data

[63] Continuation-in-part of Ser. No. 548,997, Oct. 27, 1995.
[51] Int. Cl.$^6$ .............................. C07K 1/04; C07K 1/113; C07K 2/00
[52] U.S. Cl. .......................... 530/300; 530/323; 530/333; 530/334; 530/345
[58] Field of Search ..................................... 530/300, 323, 530/333, 330, 334, 345

[56] References Cited

U.S. PATENT DOCUMENTS

| | | | |
|---|---|---|---|
| 5,200,504 | 4/1993 | Ghadiri | 530/304 |
| 5,364,851 | 11/1994 | Joran | 530/345 |
| 5,446,128 | 8/1995 | Kahn | 530/317 |
| 5,710,245 | 1/1998 | Kahn | 530/324 |

FOREIGN PATENT DOCUMENTS

WO 95/00534   1/1995   WIPO .

OTHER PUBLICATIONS

Meara et al., "Design and synthesis of small molecule initiators of α–helix structure in short peptides in water," *Chemical Abstracts 125*: 1468, Abstract No. 329432, 1996.

Beck–Sickinger et al., "Structure/activity relationships of C–terminal neuropeptide Y peptide segments and analogues composed of sequence 1–4 linked to 25–36," *Eur. J. Biochem. 194*: 449–456, 1990.

Hruby et al., "Emerging approaches in the molecular design of receptor–selective peptide ligands: conformational, topographical and dynamic considerations," *Biochem. J. 268*: 249–262, 1990.

Jung et al., "α–Helical Small Molecular Size Analogues of Neuropeptide Y: Structure–Activity Relationships," *Biopolymers 31*: 613–619, 1991.

Rose et al., "Turns in Peptides and Proteins," *Advances in Protein Chemistry 37*: 1–109, 1985.

*Primary Examiner*—Jeffrey E. Russel
*Attorney, Agent, or Firm*—Seed and Berry LLP

[57] ABSTRACT

There are disclosed alpha-helix mimetics and methods relating to the same for imparting or stabilizing alpha-helicity to a peptide or protein. In one aspect, the alpha-helix mimetics contain eleven- to fourteen-membered rings covalently attached at the end or within the length of the peptide or protein. The alpha-helix mimetics render the resulting peptide or protein more stable with regard to thermal stability, as well as making the peptide or protein more resistant to proteolytic degradation. In addition, the alpha-helix mimetics may be used in standard peptide synthesis protocols.

6 Claims, 7 Drawing Sheets

*Standard peptide synthesis, Fmoc strategy on Pam resin*

ALPHA-HELIX MIMETICS AND METHODS RELATING THERETO

RELATED APPLICATIONS

This application is a continuation-in-part of U.S. patent application Ser. No. 08/548,997, filed Oct. 27, 1995.

TECHNICAL FIELD

This invention relates generally to alpha-helix mimetics and, more specifically, to alpha-helix mimetics which stabilize the alpha-helical structure of a natural or synthetic peptide or protein.

BACKGROUND OF THE INVENTION

Proteins are polymers of amino acids in which the carbon atoms and amide groups alternate to form a linear polypeptide, with the amino acid side chains projecting from the α-carbon atom of each amino acid. The sequence of amino acids and location of disulfide bridges (if any) are considered the "primary" protein structure. The "secondary" structure of a protein refers to the steric relationship of amino acid residues that are in close proximity to one another in the linear sequence. Such steric relationships give rise to periodic structure, including the alpha-helix.

The alpha-helix is a rod-like structure wherein the polypeptide chain forms the inner part of the rod, and the side chains extend outward in a helical array. The alpha-helix is stabilized by hydrogen bonds between the NH and CO groups of the polypeptide chain. More specifically, the hydrogen of the NH group of each amino acid (i.e., amino acid residue "n") is hydrogen bonded to the oxygen of the CO group that is located four amino acid residues behind in the linear polypeptide (i.e., amino acid residue "n-4"). Such hydrogen bonding is illustrated below:

While only a single hydrogen bond is depicted above for purpose of illustration, each of the CO and NH groups of the linear polypeptide are hydrogen bonded in the alpha-helix. In particular, each amino acid is related to the next by a translation of 1.5 Å along the helix axis and a rotation of 100°, which gives 3.6 amino acid residues per turn of the alpha-helix. The pitch of the alpha-helix is 5.4 Å (the product of the translation, 1.5 Å, and the number of residues per turn, 3.6), and the diameter of the alpha-helix is 2.3 Å. The "screw sense" of the alpha-helix can be right-handed (clockwise) or left-handed (counter-clockwise). While a few left-handed alpha-helixes do exist, most alpha-helixes found in naturally occurring proteins are right-handed.

In the absence of interactions other than hydrogen-bonding, the alpha-helix is the preferred form of the polypeptide chain since, in this structure, all amino acids are in identical orientation and each forms the same hydrogen bonds. Thus, polyalanine (i.e., $[-NHCH(CH_3)CO-]_n$) exists as an alpha-helix. However, the presence of other amino acids within the polypeptide chain may cause instability to the alpha-helix. In other words, the amino acid side chains do not participate in forming the alpha-helix, and may hinder or even prevent alpha-helix formation. A striking example of such side chain dependency on alpha-helix formation is polylysine (i.e., $[-NHCH((CH_2)_4NH_2)CO-]_n$). At a pH below 10, the $NH_2$ moiety in the side chain of lysine is charged (i.e., $NH_3^+$), and electrostatic repulsion totally destroys the alpha-helix structure. Conversely, at a pH above 10, the alpha-helix structure is preferred.

The alpha-helix constitutes one of the principle architectural features of peptides and proteins, and are important structural elements in a number of biological recognition events, including ligand-receptor interactions, protein-DNA interactions, protein-RNA interactions, and protein-membrane interactions. In view of the important biological role played by the alpha-helix, there is a need in the art for compounds which can stabilize the intrinsic alpha-helix structure. There is also a need in the art for methods of making stable alpha-helix structures, as well as the use of such stabilized structures to effect or modify biological recognition events which involve alpha-helical structures. The present invention fulfills these needs and provides further related advantages.

SUMMARY OF INVENTION

Briefly stated, the present invention is directed to alpha-helix mimetics and, more specifically to alpha-helix mimetics which stabilize the alpha-helical structure of a natural or synthetic peptide or protein.

In one aspect of this invention, alpha-helix mimetics are disclosed having the following structures (Ia) and (Ib):

wherein $R^1$–$R^5$ are the same or different and independently selected from amino acid side chain moieties or derivatives thereof; W is selected from $(CH_2)_n$ and $NH(CH_2)_p$ where n is 0, 1, 2 or 3 and p is 0, 1 or 2; and X and Y represent the remainder of the molecule. Amino acid side chain moieties include, but are not limited to, the amino acid side chains of glycine, alanine, valine, leucine, isoleucine, lysine, arginine, histidine, aspartic acid, glutamic acid, asparagine, glutamine, phenylalanine, tyrosine, tryptophan, cysteine, methionine, serine and threonine. Derivatives of amino acid side chain moieties include, but are not limited to, straight chain or branched, cyclic or noncyclic, substituted or unsubstituted, saturated or unsaturated lower chain alkyl, aryl and aralkyl moieties.

In another aspect, an alpha-helix modified peptide or protein is disclosed wherein an alpha-helix mimetic of this invention is covalently attached to at least one amino acid of a peptide or protein. In this embodiment, X and/or Y in structures (Ia) and (Ib) above represent one or more amino acids of the peptide or protein. In still a further aspect, a method for imparting and/or stabilizing alpha-helicity of a peptide or protein is disclosed. This method includes covalently attaching one or more alpha-helix mimetics of this invention within, or to the end of, a peptide or protein.

Other aspects of this invention will become apparent upon reference to the attached figures and the following detailed description.

DETAILED DESCRIPTION OF THE INVENTION

As mentioned above, the alpha-helix is an important structural component for many biological recognition events. The alpha-helix mimetics of this invention serve to impart and/or stabilize the alpha-helical structure of a natural or synthetic peptide or protein, particularly with regard to thermal stability. In addition, the alpha-helix mimetics of this invention are more resistant to proteolytic breakdown, thus rendering a peptide or protein containing the same more resistant to degradation.

The alpha-helix mimetics of this invention have the following structures (Ia) and (Ib):

wherein $R_1$–$R_5$ are each selected from amino acid side chain moieties or derivatives thereof; W is selected from $(CH_2)n$ and $NH(CH_2)_p$ where n is 0, 1, 2 or 3 and p is 0, 1 or 2; and X and Y represent the remainder of the molecule. Although structures (Ia) and (Ib) have been depicted as a preferred embodiment for right-handed alpha-helices, one skilled in the art will recognize that the mirror images of structures (Ia) and (Ib) would be used in left-handed alpha-helices.

Figure 1:
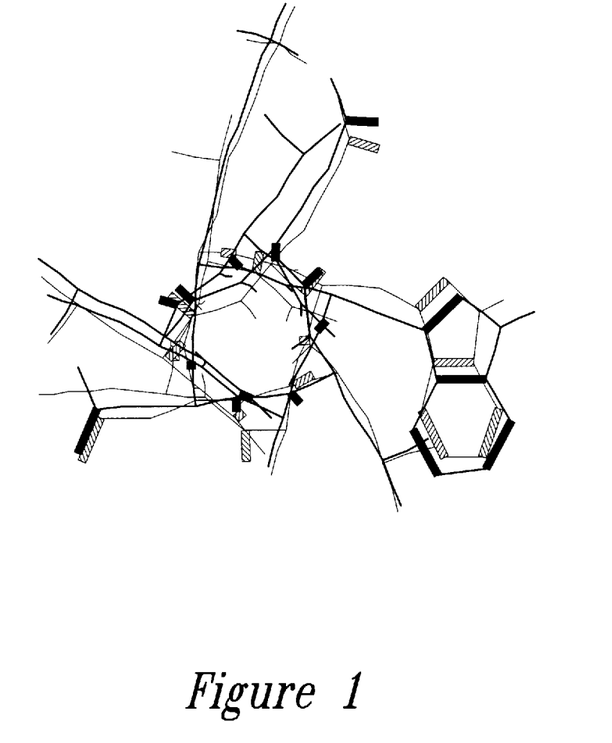
FIG. 1 is a three-dimensional representation of an alpha-helix mimetic of this invention of structure (Ia).

In three dimensions, the alpha-helix represented by structure (Ia) above is illustrated (looking down the axis of the alpha-helix) in FIG. 1 (in grey). For comparison purposes, the corresponding natural peptide is also presented (in black).

The term "remainder of the molecule", as represented by X and Y in the above structures, may be any chemical moiety. For example, when the alpha-helix mimetic is located within the length of a peptide or protein, X and Y may represent amino acids of the peptide or protein. Alternatively, if two or more alpha-helix mimetics are linked, the Y moiety of a first alpha-helix mimetic may represent a second alpha-helix mimetic while, conversely, the X moiety of the second alpha-helix mimetic represents the first alpha-helix mimetic. When the alpha-helix mimetic is located at the end of a peptide or protein, or when the alpha-helix mimetic is not associated with a peptide or protein, X and/or Y may represent a suitable terminating moiety. Such terminating moieties include, but are not limited to, —H, —OH, —OR, —NH$_2$, —CHO, —NHR and —COR (where R is a lower chain alkyl, aryl or aralkyl moiety), as well as suitable peptide synthesis protecting groups (such as BOC and FMOC).

As used herein, the term "amino acid side chain moiety" represents any amino acid side chain moiety present in naturally occurring proteins, including (but not limited to) the naturally occurring amino acid side chain moieties identified in Table 1. Other naturally occurring side chain moieties of this invention include (but are not limited to) the side chain moieties of 3,5-dibromotyrosine, 3,5-diiodotyrosine, hydroxylysine, γ-carboxyglutamate, phosphotyrosine and phosphoserine. In addition, glycosylated amino acid side chains may also be used in the practice of this invention, including (but not limited to) glycosylated serine, threonine and asparagine.

TABLE 1

| Amino Acid Side Chain Moiety | Amino Acid |
|---|---|
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_3^+$ | Lysine |
| —(CH$_2$)$_3$NHC(NH$_2$)NH$_2^+$ | Arginine |
| —CH$_2$-(imidazole, HN, N) | Histidine |
| —CH$_2$COO | Aspartic acid |
| —CH$_2$CH$_2$COO | Glutamic acid |
| —CH$_2$CONH$_2$ | Asparagine |
| —CH$_2$CH$_2$CCNH$_2$ | Giutamine |
| —CH$_2$-(phenyl) | Phenylalanine |
| —CH$_2$-(phenyl)-OH | Tyrosine |
| —CH$_2$-(indole) | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |

In addition to naturally occurring amino acid side chain moieties, the amino acid side chain moieties of the present invention also include various derivatives thereof. As used herein, a "derivative" of an amino acid side chain moiety includes modifications and/or variations to naturally occurring amino acid side chain moieties. For example, the amino acid side chain moieties of alanine, valine, leucine, isoleucine and phenylalanine may generally be classified as lower chain alkyl, aryl or aralkyl moieties. Derivatives of amino acid side chain moieties include other straight chain or branched, cyclic or noncyclic, substituted or unsubstituted, saturated or unsaturated lower chain alkyl, aryl or aralkyl moieties.

As used herein, "lower chain alkyl moieties" contain from 1–12 carbon atoms, "lower chain aryl moieties" contain from 6–12 carbon atoms, and "lower chain aralkyl moieties" contain from 7–12 carbon atoms. Thus, in one embodiment, the amino acid side chain derivative is selected from a $C_{1-12}$ alkyl, a $C_{6-12}$ aryl and a $C_{7-12}$ a-alkyl, and in a more preferred embodiment, from a $C_{1-7}$ alkyl, a $C_{6-10}$ aryl and a $C_{7-11}$ a-alkyl.

Amino acid side chain derivatives of this invention further include substituted derivatives of lower chain alkyl, aryl and aralkyl moieties, wherein the substituent is selected from (but not limited to) one or more of the following chemical moieties: —OH, —OR, —COOH, —COOR, —CONH$_2$, —NH$_2$, —NHR, —NRR, —SH, —SR, —SO$_2$R, —SO$_2$H, —SOR and halogen (including F, Cl, Br and I), wherein each occurrence of R is independently selected from a lower chain alkyl, aryl or aralkyl moiety. Moreover, cyclic lower chain alkyl, aryl and aralkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of lower chain alkyl and aralkyl moieties, including (but not limited to) alkyl and aralkyl phosphonates and silanes.

As mentioned above, the alpha-helix mimetics of this invention serve to impart and/or stabilize the alpha-helicity of a protein or peptide. The alpha-helix mimetic may be positioned at either the C-terminus or N-terminus of the protein or peptide, or it may be located within the protein or peptide itself. In addition, more than one alpha-helix mimetic of the present invention may be incorporated in a single protein or peptide.

The alpha-helix mimetics of this invention have broad utility in a variety of naturally occurring or synthetic peptides and proteins. For example, neuropeptide Y ("NPY"), a polypeptide amide of 36 amino acids, is a potent vasoconstrictor and neuromodulator, and antagonists to NPY have anti-hypertensive activity. C-terminal analogs of NPY have previously been constructed, including the following analogs: Ac—RAAANLITRQRY—NH$_2$ (SEQ ID NO: 1) and Ac—RAAANAAARQRY—NH$_2$ (SEQ ID NO: 2 ) (Ac represents that the amino-terminus is acetylated, and —NH$_2$ indicates that the carbon-terminus is an amide). The biological activity of the above analogs, as evidenced by binding to the NPY binding site, has been correlated to its alpha-helicity (see, Jung et al., *Biopolymers* 31:613–19, 1991). By substituting one or more of the alpha-helix mimetics of this invention for select amino acids within an NPY analog polypeptide, the alpha-helicity of the NPY analog may be enhanced, thus increasing its binding affinity and improving its biological activity. Suitable assays for determining bioresponse and binding are known, including the Guinea Pig Atrial Contraction Assay (Panlabs Inc., Bothell, Wash.; see also, Giuliani et al., *Br. J. Pharmacol.* 98:407–412, 1989), Discoveryscreen™ Neuropeptide Y Binding (Panlabs, Inc., Bothell, Wash.; see also, Walker et al., *Molec. Pharmacol.* 34:778–792; Saria et al., *Eur. J. Pharmacol.* 107:105–107, 1985), Rat Vas Deferens Relaxation (EFS) (Panlabs, Inc., Bothell, Wash.; see also, Wahlested et al., *Regulatory Peptide* 13:307–318, 1986;Martel et al., *J. Pharmacol. Exp. Ther.* 38:494–502, 1990) (which references are hereby incorporated by reference in their entirety).

For example, the following structures (IIa) (SEQ ID NO: 8) and (IIb) (SEQ ID NO: 8) may be made by substituting an alpha-helix mimetic of structures (Ia) and (Ib) above for the "AAAN" (SEQ ID NO: 7) sequence of the NPY analog Ac—RAAANLITRQRY—NH$_2$ (SEQ ID NO: 1):

Alternatively, more than one alpha-helix mimetic of the present invention may be utilized. For example, the following structure (III) (SEQ ID NO: 3) may be made by substituting two alpha-helix mimetics of structure (Ia) for the "AAANLITRQ" (SEQ ID NO: 4) sequence of the NPY analog Ac-RAAANLITRQRY-NH$_2$ (SEQ ID NO: 1):

(III)

A similar structure may be made by substituting two alpha-helix mimetics of structure (Ib) for the above sequence of the NPY analog. Alternatively, a combination of structures (Ia) and (Ib) may be employed.

A further example of the utility of the alpha-helix mimetics of the present invention may be illustrated with regard to cytokines. Many cytokines (e.g., hGH, IL2 and IL4) are organized into a bundle of alpha-helical structures. In many instances the C-terminal alpha-helix is a critical site of interaction with its corresponding receptor. For example, C-terminal-stabilized alpha-helical peptides (stabilized with one or more of the alpha-helix mimetics of this invention) may serve as antagonists of IL2 and IL4, and have utility as anti-inflammatory agents. More specifically, the C-terminal of both IL2 and IL4 have been found critical in ligand-receptor interaction (see, Landgraf et al., *JBC* 264:816–22, 1989; and Ramanathan et al., *Biochemistry* 32:3549–56, 1993). The respective sequences for these, regions are: [119]NRWITFCQSIISTLT[133] and (SEQ ID NO: 5) [111]NFLERLKTIMKEKYSPCS[129] (SEQ ID NO: 6). By synthesizing a peptide which contains one or more of the alpha-helix mimetics of this invention in place of certain amino acids in the above sequences, peptides can be made which will mimic the C-terminal of IL2 or IL4, thus serving as IL2 or IL4 receptor antagonists.

Furthermore, alpha-helical structures are important in recognition of DNA by many proteins (see Steitz, *Quarterly Review of Biophysics* 23:205–280, 1990). Thus, the alpha-helix mimetics of this invention may be used to synthesize transcriptional antagonists (or agonists) by disrupting the normal transcriptional element assembly (see Ho et al., *PNAS* 91:9203–07, 1994).

While the utility of the alpha-helix mimetics of this invention have been disclosed with regard to certain embodiments, it will be understood that a wide variety and type of compounds can be made which includes the alpha-helix mimetics of the present invention. For example, an alpha-helix of this invention may be substituted for two or more amino acids of a peptide or protein. In addition to improving and/or modifying the alpha-helicity of a peptide or protein, especially with regard to thermal stability, the alpha-helix mimetics of this invention also serve to inhibit proteolytic breakdown. This results in the added advantage of peptides or proteins which are less prone to proteolytic breakdown due to incorporation of the alpha-helix mimetics of this invention.

The alpha-helix mimetics of this invention may generally be synthesized on a solid support (PAM) resin from the carbonyl end to the amino end. Cyclization of resulting nascent alpha-helix mimetic may be accomplished on the solid support from the corresponding thioamide using $Hg(OOCCF_3)_2$ to effect condensation as illustrated by the following reaction yielding structure (Ia):

A similar reaction is employed to generate alpha-helix mimetics of structure (Ib). A more detailed disclosure with respect to synthesis of the alpha-helix mimetics of this invention is presented in the examples section herein below.

The alpha-helix mimetics of the present invention may be incorporated into standard peptide synthesis protocols, including automated solid phase peptide synthesis. Peptide synthesis is a stepwise process where a peptide is formed by elongation of the peptide chain through the stepwise addition of single amino acids. Amino acids are linked to the peptide chain through the formation of a peptide (amide) bond. The peptide link is formed by coupling the amino group of the peptide to the carboxylic acid group of the amino acid. The peptide is thus synthesized from the carboxyl terminus to the amino terminus. The individual steps of amino acid addition are repeated until a peptide (or protein) of desired length and amino acid sequence is synthesized.

To accomplish peptide (or protein) synthesis as described above, the amino group of the amino acid to be added to the peptide should not interfere with peptide bond formation between the amino acid and the peptide (i.e., the coupling of the amino acid's carboxyl group to the amino group of the peptide). To prevent such interference, the amino group of the amino acids used in peptide synthesis are protected with suitable protecting groups. Typical amino protecting groups include BOC and FMOC groups. Accordingly, in one embodiment of the present invention, the alpha-helix mimetics of the present invention bear a free carboxylic acid group and a protected amino group, and are thus suitable for incorporation into a peptide by standard synthetic techniques.

The following examples are offered by way of illustration, not limitation.

EXAMPLES

Example 1

General Synthesis of Alpha-Helix Mimetics of Structure (Ia)

Figure 2:
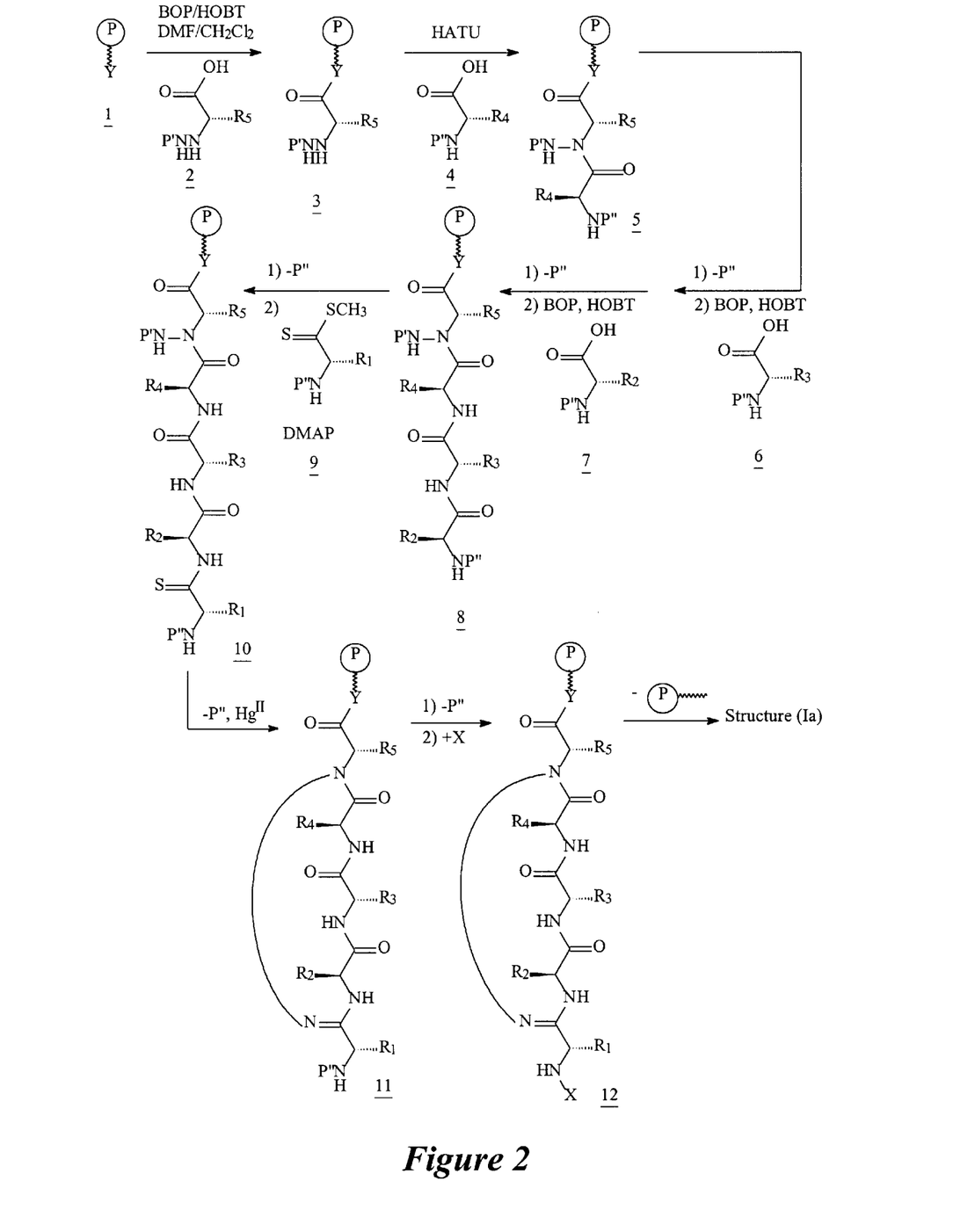
FIG. 2 illustrates the general synthesis of alpha-helix mimetics of this invention of structure (Ia).

This example illustrates the general synthesis of alpha-helix mimetics of this invention having structure (Ia) above. Referring to FIG. 2, Y moiety attached to solid support (1) is linked by an appropriate covalent bond to an N-protected hydrazine bearing $R_5$ (2) to yield (3). Through a series of additions, first employing an N-protected acid bearing $R_4$ (4) to produce (5), followed by addition of N-protected amino acids bearing $R_3$ and $R_2$, (6) and (7), respectively, the peptide backbone is extended to yield (8). An N-protected thioamide bearing $R_1$ (9) is then added to yield nascent alpha-helix mimetic (10), which is then cyclized to effect condensation and yield an N-protected alpha-helix mimetic bound to solid support (11). A desired X moiety may then be added to yield (12) by an appropriate covalent bond, followed by cleavage from the solid support to generate an alpha-helix mimetic of structure (Ia).

Example 2

General Synthesis of Alpha-Helix Mimetics of Structure (Ib)

Figure 3A:
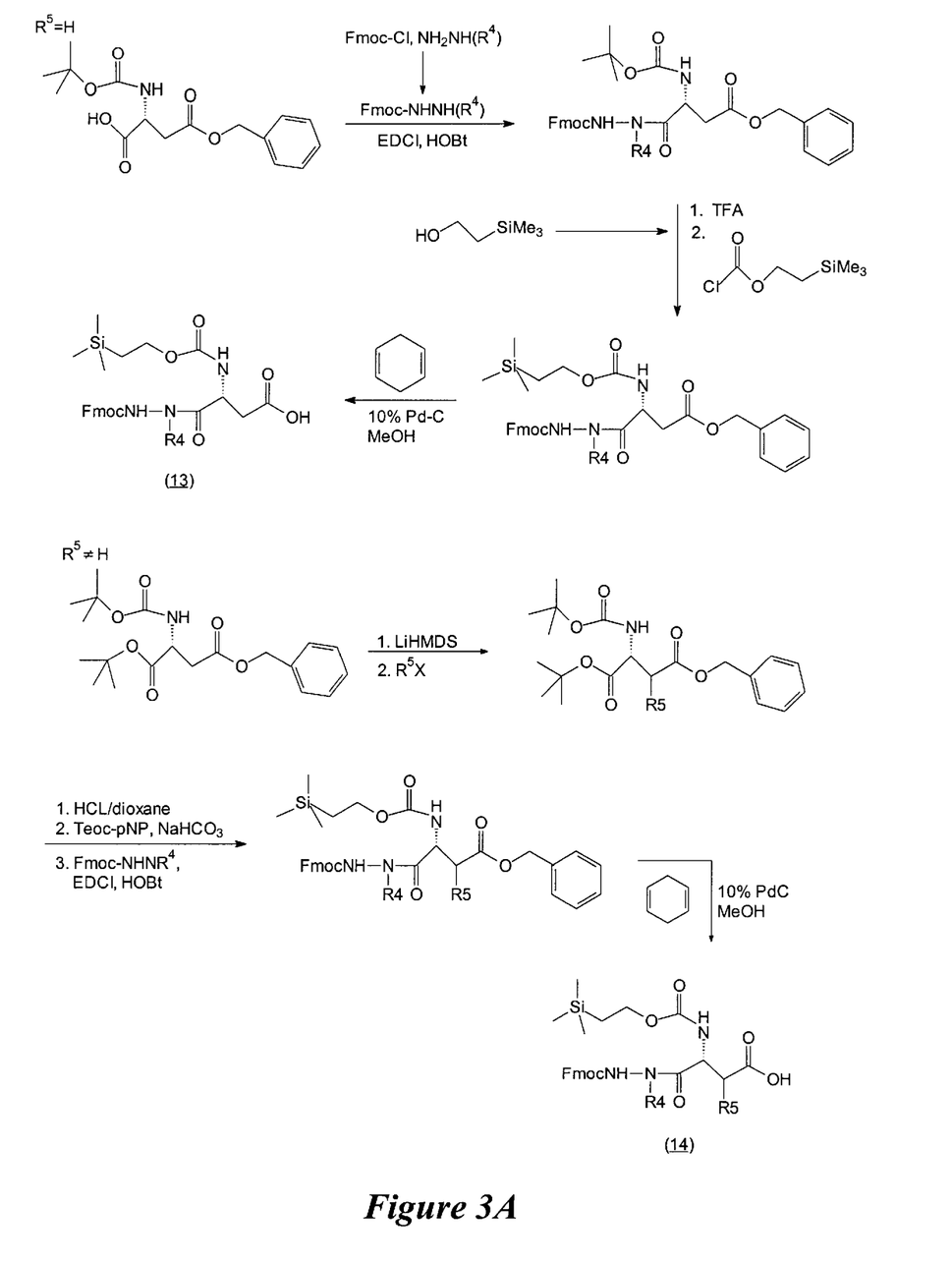
FIGS. 3A, 3B and 4 illustrate the general synthesis of alpha-helix mimetics of this invention of structure (Ib).
Figure 3B:
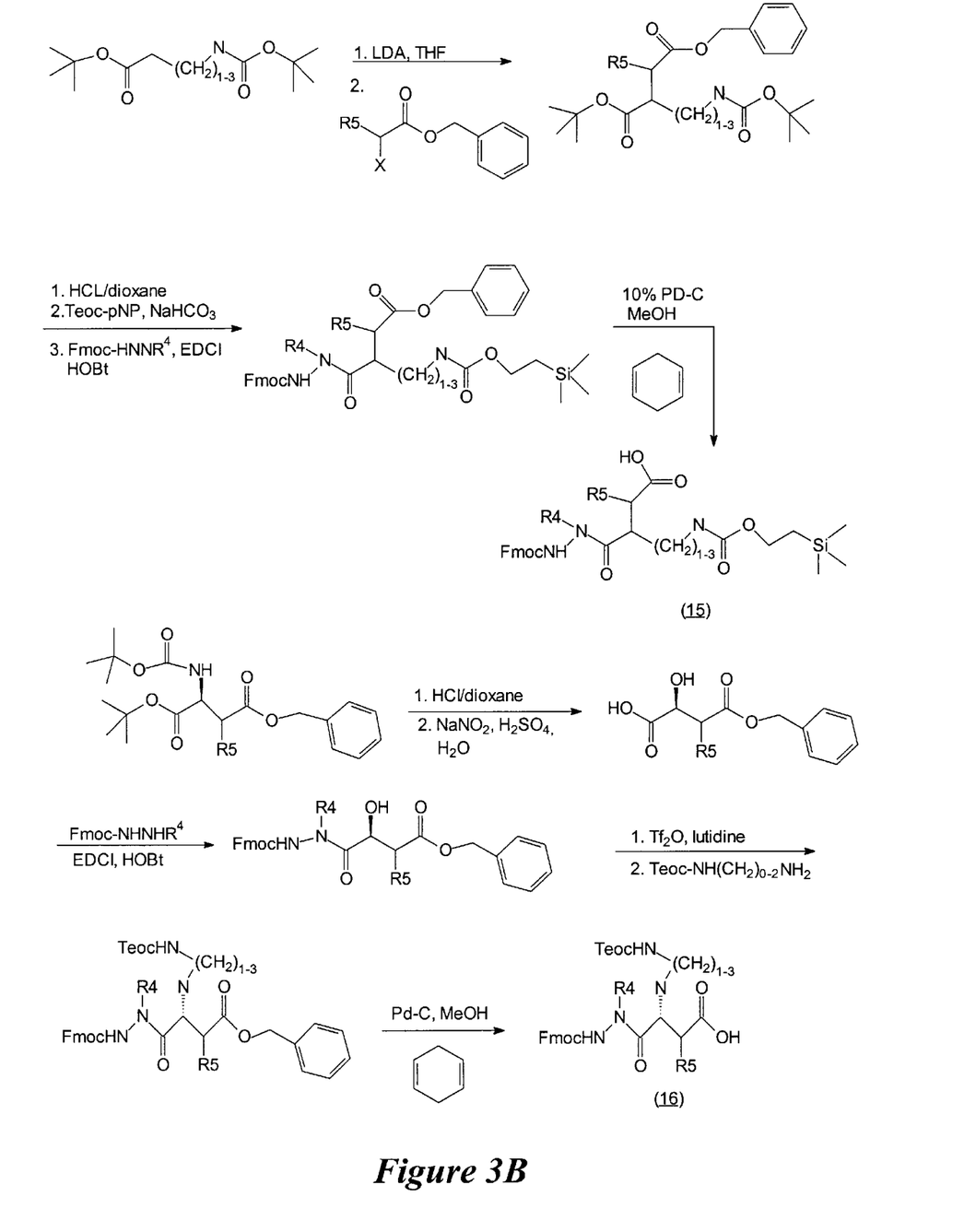

This example illustrates the general synthesis of alpha-helix mimetics of this invention having structure (Ib) above. W-bearing hydrazine intermediates of structure (13), (14), (15) or (16) are prepared by the procedures disclosed in FIGS. 3A and 3B.

Figure 4:
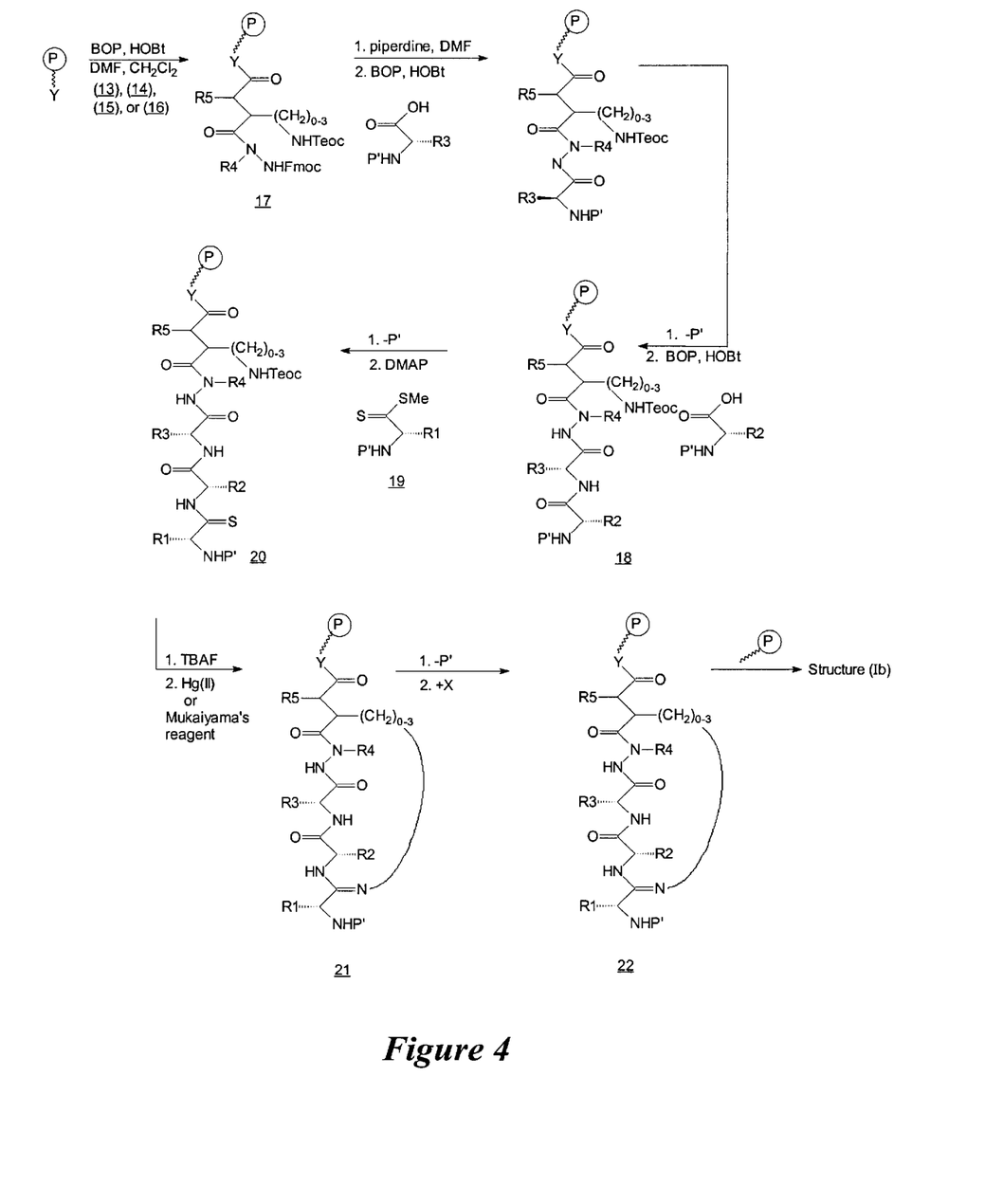

Referring to FIG. 4, Y moiety attached to solid support is linked by an appropriate covalent bond to (13), (14), (15) or (16) to yield (17). Through a series of additions, the peptide backbone is extended to yield (18). An N-protected thioamide (19) is then added to yield nascent alpha-helix mimetic (20), which is then cyclized to effect condensation and yield N-protected alpha-helix mimetic bound to solid support (21). A desired X moiety is then added to yield (22), followed by cleavage from the solid support to generate an alpha-helix mimetic of structure (Ib).

Example 3

Synthesis of a Representative Peptide Containing an Alpha-Helix Mimetic

This example illustrates the synthesis of a representative alpha-helix mimetic of this invention having the following structure (IV) (SEQ ID NO 3):

Structure (IV) may be synthesized on PAM resin using an Advanced Chemtech ACT 90 model synthesizer. Couplings may be conducted using 1-hydroxybenzotriazole, benzotriazolyl-oxy-tris-(dimethylamino) phosphonium hexafluorophosphate, and diisopropylethylamine in a mixture of NMP at room temperature. Cleavage from the resin may be accomplished with DBU/THF/$H_2O$ or ammonolysis. The resin may be extracted with aqueous THF or dilute acetic acid and evaporated to dryness in vacuo. The crude product may be purified by reverse phase C18 high performance liquid chromatography.

Figure 5A:
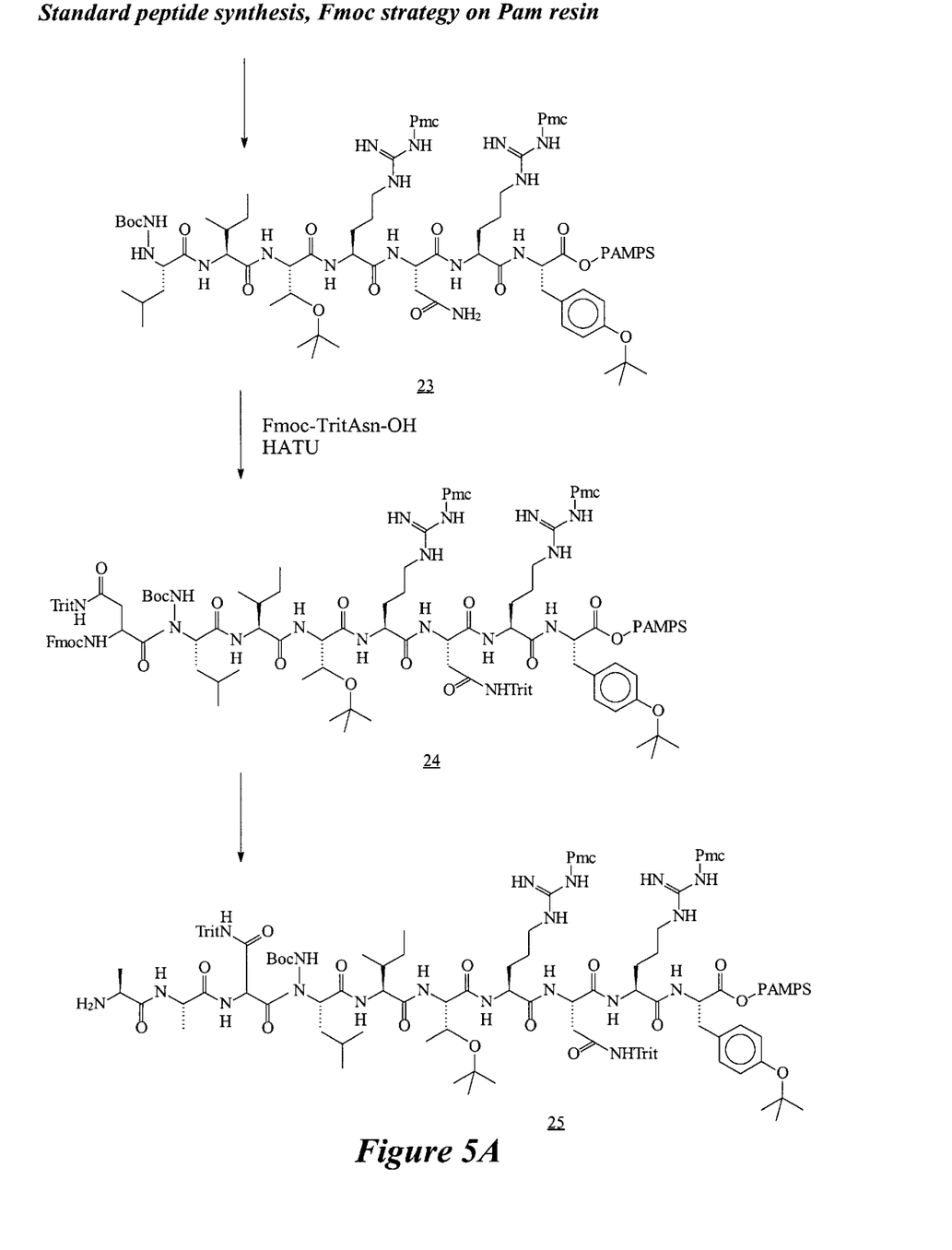
FIGS. 5A and 5B illustrates the synthesis of a representative alpha-helix mimetic of this invention.
Figure 5B:
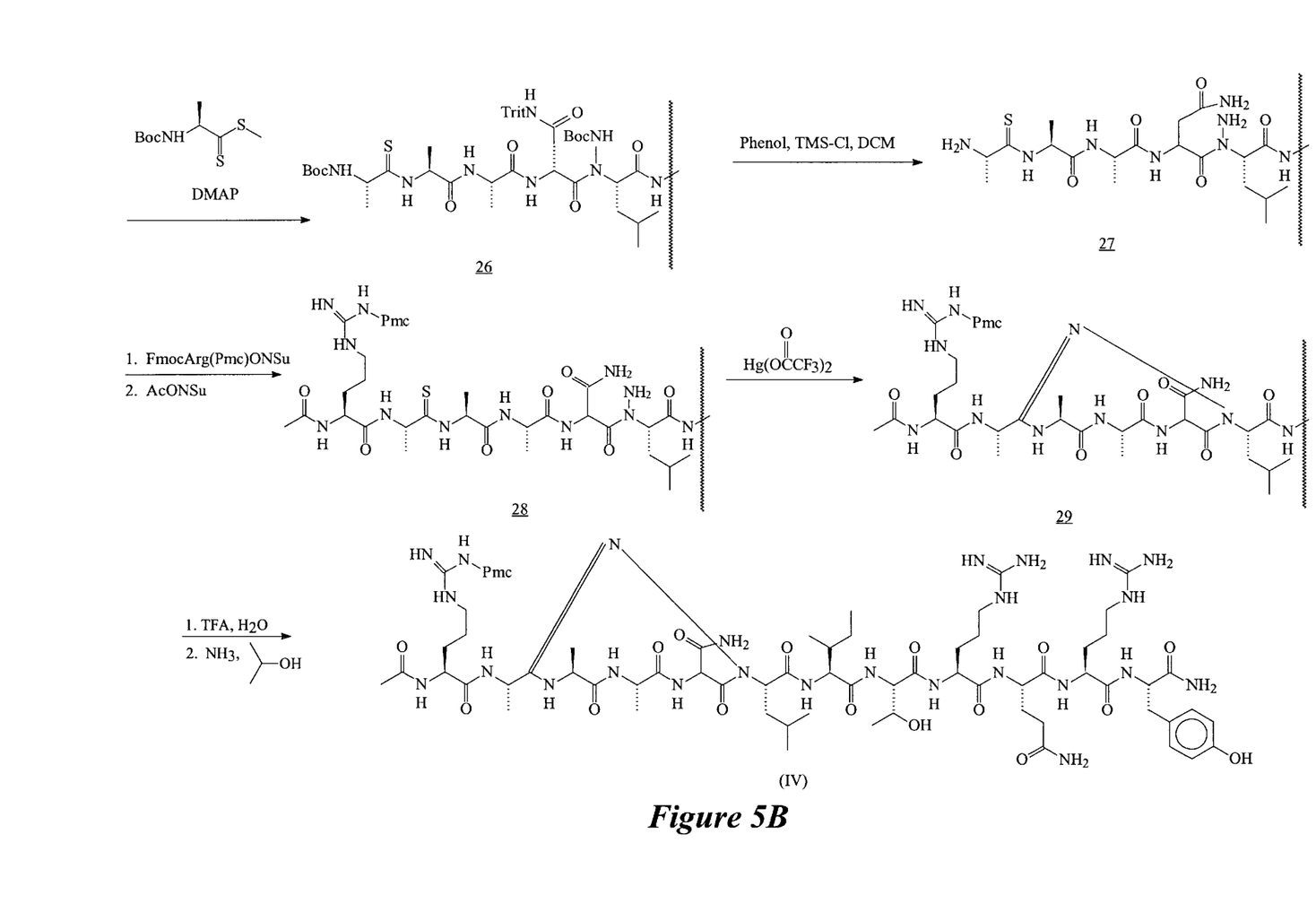

More specifically, structure (IV) is synthesized as illustrated in FIGS. 5A and 5B. The Fmoc deprotection is accomplished using piperidine in DMF (25% solution, 12 minutes). For coupling, a mixture of amino acid BOP—HOBt—DIEA (3:3:3:4 eq.) in NMP is used. For coupling of Fmoc—TritylAsn—OH to hydrazine (23→24), a mixture of Fmoc—TritylAsn—OH:HATU:DIEA (6:6:9 eq.), in NMP, (3 ml for 1 mmol of Gly) is employed. By standard peptide coupling techniques two additional alanine moieties were added to yield (25). Formation of thioamide (26) is achieved by treatment of (25) with BocAla—SMe (5 eq.) in the presence of $CF_3CO_2Cs$ (3 eq.) and DMAP (1eq.) in a mixture of DMF:DCM (1:1) for 12 hours. Deprotection of t-Butyl based protecting groups (26→27) is performed with TMS—Cl (1M) and phenol (3M) in DCM for 30 minutes (see, e.g., Kaiser et al., *JOC* 58:5167–75, 1993). Structure (27) is coupled to FmocArg(Pmc), deprotected and then acetylated to yield (28). Cyclization is affected by suspending the precyclized material (28) in dichloromethane and treating this material with 1.1 equivalents of Hg(OC(=O)$CF_3)_2$ for 4 hours at room temperature to yield (29), which is removed from the solid support to yield structure (IV).

Example 4

Alpha-Helicity of a Representative Peptide Containing an Alpha-Helix Mimetic This example illustrates the enhanced alpha-helicity of a peptide containing a representative alpha-helix mimetic of the present invention.

Alpha-helicity of a peptide is typically determined by measuring its circular dichroism (CD), and CD data is normally presented as mean residue ellipticies $[\Theta]_m$. Alpha-helical peptides show two negative Cotton effects at 208 nm and 222 nm, and a positive Cotton effect at 193 nm, while the CD spectra of peptides with random coil secondary structure are dominated by the increasing negative Cotton effect at shorter wavelength. Alpha-helicity may be estimated from the value at 222 nm, and by comparing the negative Cotton effects at 222 nm and 208 nm. Increasing (IV)

fraction of $[\Theta]_m(222 \text{ nm})$ divided by $[\Theta]_m(208 \text{ nm})$ correlates with increasing alpha-helicity. High values for $[\Theta]_m(208 \text{ nm})$ compared to $[\Theta]_m(222 \text{ nm})$ and a shifting minimum from 208 nm to shorter wavelengths indicate random coil conformation.

An NPY analog having the structure Ac-RAAANLITRQRY-NH$_2$ (SEQ ID NO: 1) is synthesized according to standard solid phase peptide synthetic techniques. The NPY analog is then dissolved in water at a concentration of 75 μM, and its CD measured using a JASCO J500 CD spectrometer at a temperature of both 3° C. and 25° C.

Structure (IV) is synthesized according to Examples 1 and 3, and its CD is similarly measured at both 30° C. and 25° C. (at a concentration of 75 μM).

The alpha-helicity of the NPY analog is enhanced by the substitution of an alpha-helix mimetic of this invention within the peptide sequence. Since biological activity of the NPY analog has been correlated to alpha-helicity, the ability of the alpha-helix mimetics of this invention to enhance alpha-helicity will correspondingly enhance the biological activity of the NPY analog containing the alpha-helix mimetic.

Example 5

Stability of a Representative Peptide Containing an Alpha-Helix Mimetic

This example illustrates that the alpha-helix mimetics of this invention are more resistant to proteolytic breakdown, thus rendering a peptide or protein containing the same more resistant to degradation.

As discussed above, NPY is a polypeptide of 36 amino acids. It is widely distributed throughout both the peripheral and central nervous systems, and is by far the most abundant peptide in the mammalian brain. NPY exerts a wide variety of physiological effects, including modulation of smooth muscle tone, hormone secretion and ion transport in the periphery, regulation of feeding behavior, locomotor activity, sexual activity, heart and respiratory rates, as well as learning and memory in the central nervous system. Given these diverse roles, NPY has been implicated in several pathophysiological conditions including hypertension, congenetive heart failure, locomotor disorders such as Parkinson's disease and Huntington's chorea, and physiological disorders such as anorexia nervosa, depression and Alzheimer's disease (Dumont et al., *Progress in Neurobiology* 38:125–167, 1992; Heilig and Widerlöv, *Acta. Psychiatr. Scand.* 82:95–114, 1990). More specifically, NPY is a known a potent vasoconstrictor and neuromodulator, and antagonists to NPY have known anti-hypertensive activity (Walker et al., *Trends in Pharmacological Sciences*, pp. 111–115, 1991).

C-terminal analogs of NPY have previously been constructed, and the biological activity of such analogs has been correlated to alpha-helicity (Jung et al., *Biopolymers* 31:613–19, 1992; Doughty and Hu, *Biopolymers* 33:1195–1206, 1993). In the practice of the present invention, one or more alpha-helix mimetics may be substituted for selected amino acids within the NPY analog peptide. Such substitutions results in NPY analog peptides having greater resistance to proteolytic breakdown than the NPY peptide absent the alpha-helix mimetic.

To illustrate this point, the following experiment is performed which demonstrates the enhanced resistance to proteolytic breakdown of NPY containing an alpha-helix mimetic of this invention, over that of the NPY peptide itself. In this experiment, the proteolytic enzyme is elastase. Elastase is a widely distributed protease (e.g., pancreas, leukocytes, lung) of broad specificity capable of hydrolyzing proteins at the C-terminal of peptide bonds of aliphatic residues. Elastase degrades elastin (the protein of elastic fiber) as well as other proteins (such as fibrin, hemoglobin and albumin), and is a serine protease which is structurally related (i.e., 39% homology) to chymotrypsin.

Structure (IV) is synthesized according the Examples 1 and 3 above and is assayed for its resistance to attack by elastase. The elastase assay employed in this experiment is based on the paper by Boudier et al. (*Biochemical Medicine* 23:210–222, 1967), and is a modification of the assay described by Groll and Thomas (*Analytical Biochemistry* 19:211–225, 1967).

In this assay, structure (IV) and the NPY analog of Example 3 (i.e., Ac—RAAANLITRQRY—NH$_2$) (SEQ ID NO:1) at a concentration of $2 \times 10^{-3}$M are separately incubated with 0.56 units of porcine pancreatic elastase in the presence of 200 mM NaCl in 100 mM Tris-HCl buffer (pH 8.5) at 37° C. At 2, 5, 10 and 20 minutes, the reactions are quenched by addition of AcOH. The cleavage activities were measured using HPLC (C18 reverse-phase column) monitored at 214 nm with a linear gradient 0 to 45% acetonitrile over 20 minutes. Half life is measured by graphing the disappearance of starting material (as judged by the decrease in integrated area under the peak) versus time.

The representative alpha-helix mimetic has significantly increased resistance to proteolytic degradation compared to that of the NPY analog.

Example 6

Biological Activity of a Representative Peptide Containing an Alpha-Helix Mimetic This example compares the biological activity of a peptide having known activity to the activity of the same peptide having one or more of the alpha-helix mimetics of this invention substituted for selective amino acids of the peptide.

In this experiment, the biological activity (i.e., receptor binding) of an NPY analog peptide to that of a NPY peptide containing an alpha-helix mimetic of this invention is compared. Specifically, both the NPY analog and structure (IV) of Example 5 above are assayed for their receptor binding affinity in a rabbit kidney membrane preparation as described by Walker and Miller (*J. Mol. Pharmacol.* 34:779–792, 1988).

This assay measures receptor binding affinity in a rabbit kidney membrane preparation. Membranes prepared from male rabbit kidney medullae are incubated with 0.2 nM [$^3$H]neuropeptide Y for 30 minutes at 22° C. Non-specific binding is determined in the presence of 0.26 μM native neuropeptide Y. Bound [$^3$H]neuropeptide Y is separated from free radioligand by rapid filtration through glass fiber filtermats and subsequently washed 3 times. Filtermats are then counted in a LKB Betaplate to determine specifically bound [$^3$H]neuropeptide Y.

The NPY analog and structure (IV) exhibits significant activity. Since the NPY analog peptide is biologically active, structure (IV) is expected to have the same or similar in vivo activity.

From the foregoing, it will be appreciated that, although specific embodiments of this invention have been described herein for purposes of illustration, various modifications may be made without deviating from the spirit and scope of the invention. Accordingly, the invention is not limited except by the appended claims.

---

We claim:

1. An alpha-helix mimetic having the structure:

wherein $R^1$ through $R^5$ are independently selected from an amino acid side chain moiety and derivative thereof; W is selected from $(CH_2)_n$ and $NH(CH_2)_p$ where n is 0, 1, 2 or 3 and p is 0, 1 or 2; and X and Y represent the remainder of the mimetic.

2. The alpha-helix mimetic of claim 1 wherein the amino acid side chain moiety is selected from the amino acid side chains of glycine, alanine, valine, leucine, isoleucine, lysine, arginine, histidine, aspartic acid, glutamic acid, asparagine, glutamine, phenylalanine, tyrosine, tryptophan, cysteine, methionine, serine and threonine.

3. An alpha-helix modified peptide or protein, comprising a peptide or protein and an alpha-helix mimetic, the alpha-helix mimetic being covalently attached to at least one amino acid of the peptide or protein, wherein the alpha-helix mimetic has the structure:

wherein $R^1$ through $R^5$ are independently selected from an amino acid side chain moiety and derivative thereof; W is selected from $(CH_2)_n$ and $NH(CH_2)_p$ where n is 0, 1, 2 or 3 and p is 0, 1 or 2; and at least X or Y is an amino acid of the peptide or protein.

4. The peptide or protein of claim 3 wherein both X and Y are amino acids of the peptide or protein.

5. A method for imparting or stabilizing alpha-helicity to a peptide or protein, comprising covalently attaching an alpha-helix mimetic to the peptide or protein, wherein the alpha-helix mimetic has the structure:

wherein $R^1$ through $R^5$ are independently selected from an amino acid side chain moiety and derivative thereof; W is selected from $(CH_2)_n$ and $NH(CH_2)_p$ where n is 0, 1, 2 or 3 and p is 0, 1 or 2; and at least X or Y represent an amino acid of the peptide or protein.

6. The method of claim 5 wherein both X and Y are amino acids of the peptide or protein.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear     ( x i ) SEQUENCE DESCRIPTION: SEQ ID NO:1:

Arg  Ala  Ala  Ala  Asn  Leu  Ile  Thr  Arg  Gln  Arg  Tyr
    1                  5                           1 0

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear     ( x i ) SEQUENCE DESCRIPTION: SEQ ID NO:2:

Arg  Ala  Ala  Ala  Asn  Ala  Ala  Ala  Arg  Gln  Arg  Tyr
    1                  5                           1 0

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear     ( i x ) FEATURE:
        ( A ) NAME/KEY: Modified-site
        ( B ) LOCATION: 2
        ( D ) OTHER INFORMATION: /note= "Xaa is Leu wherein a
            nitrogen is substituted for the double bonded oxygen to
            form a imine group"

( x i ) SEQUENCE DESCRIPTION: SEQ ID NO:3:

Arg  Xaa  Ala  Ala  Asn  Leu  Ile  Thr  Arg  Gln  Arg  Tyr
    1                  5                           1 0

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear     ( x i ) SEQUENCE DESCRIPTION: SEQ ID NO:4:

Ala  Ala  Ala  Asn  Leu  Ile  Thr  Arg  Gln
    1                  5

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( C ) STRANDEDNESS:

```
              ( D ) TOPOLOGY: linear ( x i ) SEQUENCE DESCRIPTION: SEQ ID NO:5:

Asn   Arg   Trp   Ile   Thr   Phe   Cys   Gln   Ser   Ile   Ile   Ser   Thr   Leu   Thr
        1                       5                             10                            15

( 2 ) INFORMATION FOR SEQ ID NO:6:

( i ) SEQUENCE CHARACTERISTICS:
              ( A ) LENGTH: 19 amino acids
              ( B ) TYPE: amino acid
              ( C ) STRANDEDNESS:
              ( D ) TOPOLOGY: linear ( x i ) SEQUENCE DESCRIPTION: SEQ ID NO:6:

Asn   Phe   Leu   Glu   Arg   Leu   Lys   Thr   Ile   Met   Arg   Glu   Lys   Tyr   Ser   Pro
        1                       5                             10                            15

Cys   Ser   Ser ( 2 ) INFORMATION FOR SEQ ID NO:7:

( i ) SEQUENCE CHARACTERISTICS:
              ( A ) LENGTH: 4 amino acids
              ( B ) TYPE: amino acid
              ( C ) STRANDEDNESS:
              ( D ) TOPOLOGY: linear ( x i ) SEQUENCE DESCRIPTION: SEQ ID NO:7:

Ala   Ala   Ala   Asn
        1

( 2 ) INFORMATION FOR SEQ ID NO:8:

( i ) SEQUENCE CHARACTERISTICS:
              ( A ) LENGTH: 7 amino acids
              ( B ) TYPE: amino acid
              ( C ) STRANDEDNESS:
              ( D ) TOPOLOGY: linear ( x i ) SEQUENCE DESCRIPTION: SEQ ID NO:8:

Leu   Ile   Thr   Arg   Gln   Arg   Tyr
        1                       5
```